US009611297B1

(12) United States Patent
Leger et al.

(10) Patent No.: US 9,611,297 B1
(45) Date of Patent: Apr. 4, 2017

(54) COMPOSITIONS AND METHODS FOR THE TREATMENT OF CAST NEPHROPATHY AND RELATED CONDITIONS

(71) Applicant: Thrasos Therapeutics Inc., Montreal (CA)

(72) Inventors: Roger Leger, Saint-Lambert (CA); Gilles Dube, Beaconsfield (CA); Marie-Elaine Caruso, Montreal (CA); Jerome Rossert, Nahant, MA (US)

(73) Assignee: Thrasos Therapeutics Inc., Montreal (CA)

( * ) Notice: Subject to any disclaimer, the term of this patent is extended or adjusted under 35 U.S.C. 154(b) by 0 days.

(21) Appl. No.: 15/368,260

(22) Filed: Dec. 2, 2016

Related U.S. Application Data

(60) Provisional application No. 62/380,068, filed on Aug. 26, 2016.

(51) Int. Cl.
| | | |
|---|---|---|
| *C07K 1/00* | (2006.01) | |
| *C07K 14/00* | (2006.01) | |
| *C07K 17/00* | (2006.01) | |
| *A61K 38/12* | (2006.01) | |
| *C07K 7/08* | (2006.01) | |
| *A61K 38/00* | (2006.01) | |

(52) U.S. Cl.
CPC ............... *C07K 7/08* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,141,389 B1 | 11/2006 | Nakamura et al. | |
| 7,244,613 B2 | 7/2007 | Gicquel et al. | |
| 7,332,569 B2 | 2/2008 | Cojocaru et al. | |
| 7,553,944 B2 | 6/2009 | Yuen et al. | |
| 7,790,862 B2 * | 9/2010 | Lewis ................. | C07K 16/244 530/351 |
| 7,939,634 B2 | 5/2011 | Ayalon-Soffer et al. | |
| 8,092,994 B2 | 1/2012 | Yuen et al. | |
| 8,343,764 B2 | 1/2013 | Abad et al. | |
| 8,541,208 B1 | 9/2013 | Plesch et al. | |
| 9,051,550 B2 | 6/2015 | Lancaster et al. | |
| 2004/0031072 A1 | 2/2004 | La Rosa et al. | |
| 2004/0123343 A1 | 6/2004 | La Rosa et al. | |
| 2004/0214165 A1 | 10/2004 | Gicquel et al. | |
| 2004/0214272 A1 | 10/2004 | La Rosa et al. | |
| 2005/0107296 A1 | 5/2005 | Merkoulova-Rainon | |
| 2005/0158714 A9 | 7/2005 | Gicquel et al. | |
| 2005/0277156 A1 | 12/2005 | Cojocaru et al. | |
| 2006/0018923 A1 | 1/2006 | Yuen et al. | |
| 2007/0015173 A1 | 1/2007 | Gicquel et al. | |
| 2007/0061916 A1 | 3/2007 | Kovalic et al. | |
| 2007/0124833 A1 | 5/2007 | Abad et al. | |
| 2008/0148432 A1 | 6/2008 | Abad | |
| 2008/0182299 A1 | 7/2008 | Colocaru et al. | |
| 2009/0087878 A9 | 4/2009 | La Rosa et al. | |
| 2009/0169473 A1 | 7/2009 | Nishimura et al. | |
| 2009/0305282 A1 | 12/2009 | Yuen et al. | |
| 2010/0017904 A1 | 1/2010 | Abad et al. | |
| 2010/0075891 A1 | 3/2010 | Ayalon-Soffer et al. | |
| 2010/0269213 A2 | 10/2010 | La Rosa et al. | |
| 2011/0131679 A2 | 6/2011 | La Rosa et al. | |
| 2011/0212051 A1 | 9/2011 | Ayalon-Soffer et al. | |
| 2011/0214205 A1 | 9/2011 | Dietrich et al. | |
| 2012/0017292 A1 | 1/2012 | Kovalic et al. | |
| 2012/0128637 A1 | 5/2012 | Lancaster et al. | |
| 2013/0031672 A1 | 1/2013 | Flasinski et al. | |
| 2013/0152224 A1 | 6/2013 | Abad et al. | |
| 2013/0276169 A1 | 10/2013 | Poraty et al. | |
| 2014/0178950 A1 | 6/2014 | Franklin et al. | |
| 2014/0325709 A1 | 10/2014 | Plesch et al. | |
| 2015/0113680 A1 | 4/2015 | Kovalic et al. | |
| 2015/0184189 A1 | 7/2015 | Abad et al. | |
| 2015/0266939 A1 | 9/2015 | Vogan et al. | |
| 2015/0328367 A1 | 11/2015 | Lancaster et al. | |

FOREIGN PATENT DOCUMENTS

| | | |
|---|---|---|
| WO | 9909186 A2 | 2/1999 |
| WO | 0157182 A2 | 8/2001 |
| WO | 0179449 A2 | 10/2001 |
| WO | 02090491 A2 | 11/2002 |
| WO | 03038095 A | 5/2003 |
| WO | 2005072055 A2 | 8/2005 |
| WO | 2005072340 A2 | 8/2005 |
| WO | 2006007795 A1 | 1/2006 |
| WO | 2006054297 A2 | 5/2006 |

(Continued)

OTHER PUBLICATIONS

Asao et al., "The amino acid sequence of a Bowman-Birk type proteinase inhibitor from faba beans (*Vicia faba* L.)," Journal of Biochemistry. 110(6):951-5 (1991).

Barsyte et al., "Cloning and characterization of metallothionein cDNAs in the mussel *Mytilus edulis* L. digestive gland," Comparative Biochemistry and Physiology, Part C: Pharmacology, Toxicology, & Endocrinology. 122C(2): 287-96 (1999).

Bigot et al., "Metallothionein coding sequence identification and seasonal mRNA expression of detoxification genes in the bivalve *Corbicula fluminea*," Ecotoxicology and Enviromental Safety. 72(2): 382-7 (2009).

David et al., "Characterisation and genetic polymorphism of metallothionein gene CgMT4 in experimental families of Pacific oyster *Crassostrea gigas* displaying summer mortality," Biomarkers. 17(1): 85-95 (2012).

Domoney et al., "Multiple isoforms of Pisum trypsin inhibitors result from modification of two primary gene products," FEBS Letters. 360(1): 15-20 (1995).

Dondero et al., "Quantitative PCR analysis of two molluscan metallothionein genes unveils differential expression and regulation," Gene. 345(2): 259-70 (2005).

(Continued)

*Primary Examiner* — Olga N Chernyshev
(74) *Attorney, Agent, or Firm* — McCarter & English, LLP; Jonathan M. Sparks; Michael J. DeGrazia

(57) ABSTRACT

Provided are novel peptides of Formula SEQ ID No. 1:

$J^1CysX^1X^2X^3X^4X^5X^6ProX^7ThrCysJ^2J^3(J^4)_s(J^5)_t$;   (SEQ ID No. 1)

pharmaceutically acceptable salts thereof, and pharmaceutical compositions thereof, which are effective inhibitors of light chains to uromodulin.

3 Claims, 4 Drawing Sheets

(56) References Cited

FOREIGN PATENT DOCUMENTS

| WO | 2006/069610 A2 | 7/2006 |
|---|---|---|
| WO | 2006138005 A2 | 12/2006 |
| WO | 2007049620 A1 | 5/2007 |
| WO | 2007/087815 A2 | 8/2007 |
| WO | 2010083178 A1 | 7/2010 |
| WO | 2010118352 A1 | 10/2010 |
| WO | 2011088299 A1 | 7/2011 |
| WO | 2012085862 A2 | 6/2012 |
| WO | 2013138795 A1 | 9/2013 |
| WO | 2014089514 A1 | 6/2014 |

OTHER PUBLICATIONS

Ferrasson et al., "Amino acid sequence of a Bowman-Birk proteinase inhibitor from pea seeds," Journal of Protein Chemistry. 14(6): 467-75 (1995).

Fontana et al., "Cerato-platanin treated plane leaves restrict Ceratocystis platani growth and overexpress defense-related genes," Journal of Plant Pathology. 90(2): 295-306 (2008).

Hardivillier et al., "Do organisms living around hydrothermal vent sites contain specific metallothioneins? The case of the genus *Bathymodiolus* (Bivalvia, Mytilidae)," Comparative Biochemistry and Physiology, Part C: Toxicology & Pharmacology. 139C(1-3): 111-8 (2004).

Jenny et al., "Diversity of metallothioneins in the American oyster, *Crassostrea virginica* revealed by the transcriptomic and proteomic approaches," European Journal of Biochemistry. 271(9): 1702-12 (2004).

Jenny et al., "Regulation of metallothionein genes in the American oyster (*Crassostrea virginica*): Ontogeny and differential expression in response to different stressors," Gene. 379: 156-65 (2006).

Khoo et al., "Metallothionein cDNA, promoter, and genomic sequences of the tropical green mussel, *Perna viridis*," Journal of Experimental Zoology. 284(4): 445-53 (1999).

Ladhar-Chaabouni et al., "Cloning and characterization of cDNA probes for the analysis of metallothionein gene expression in the Mediterranean bivalves: Ruditapes decussatus and Cerastoderma glaucum," Molecular Biology Reports. 36(5): 1007-14 (2009).

Leignel et al., "Isolation and characterization of Mytilus edulis metallothionein genes," Comparative Biochemistry and Physiology, Part C: Toxicology & Pharmacology. 142C(1-2): 12-18 (2006).

Leignel et al., "Small metallothionein MT-10 genes in coastal and hydrothermal mussels," Marine Biotechnology. 7(3): 236-44 (2005).

Lemoine et al., "Metallothionein isoforms in mytilus edulis (Mollusca, Bivalvia): complementary DNA characterization and quantification of expression in different organs after exposure to cadmium, zinc, and copper," Marine Biotechnology 2(2): 195-203 (2000).

Liu et al., "Two metallothionein genes in Oxya chinensis: molecular characteristics, expression patterns and roles in heavy metal stress," PLoS One. 9(11): e112759/1-10 (2014).

Lynch et al., "Genomic analysis and relatedness of P2-like phages of the Burkholderia cepacia complex," BMC Genomics 11 <biomedcentral.com/content/pdf/1471-2164-11-599.pdf> (2010).

Mackay et al., "Complete amino acid sequences of five dimeric and four monomeric forms of metallothionein from the adible mussel *Mytilus edulis*," European Journal of Biochemistry. 218(1):183-94 (1993).

Orihuela et al., "The metal-binding features of the recombinant mussel *Mytilus edulis* MT-10-IV metallothionein," Journal of Biological Inorganic Chemistry. 13(5): 801-12 (2008).

Page et al., "Combinatorial variation in coding and promoter sequences of genes at the Tri locus in Pisum sativum accounts for variation in trypsin inhibitor activity in seeds," Molecular Genetics and Genomics. 267(3): 359-69 (2002).

Quillien et al., "Protease inhibitors from pea seeds: biochemical characteristics," Plant Proteins from European Crops, ed. Gueguen, Jacques et al. Springer, Germany. 26-30 (1998).

Quillien et al., "Trypsin inhibitor polymorphism: multigene family expression and posttranslational modification," Journal of Protein Chemistry. 16(3): 195-203 (1997).

Rahbe et al., "Toxicity to the pea aphid *Acyrthosiphon pisum* of anti-chymotrypsin isoforms and fragments of Bowman-Birk protease inhibitors from pea seeds," Insect Biochemistry and Molecular Biology. 33(3): 299-306 (2003).

Ribeiro et al., "An annotated catalog of salivary gland transcripts from *Ixodes scapularis* ticks," Insect Biochemistry and Molecular Biology. 36(2): 111-29 (2006).

Tanguy et al., "Metallothionein genes in the European flat oyster *Ostrea edulis*: a potential ecological tool for environmental monitoring?" Marine Ecology: Progress Series. 257: 87-97 (2003).

Unger et al., "Primary structure of molluskan metallthioneins deduced from PCR-amplified cDNA and mass spectrometry of purified proteins," Biochimica et Biophysica Acta, General Subjects. 1074(3): 371-7 (1991).

Weder et al., "Complete amino acid sequence of the lentil trypsin-chymotrypsin inhibitor LCI-1.7 and a discussion of atypical binding sites of bowman-birk inhibitors," Journal of Agricultural and Food Chemistry. 52(13): 4219-26 (2004).

Xu et al., "Identification of expressed genes in cDNA library of hemocytes from the RLO-challenged oyster, *Crassostrea ariakensis* Gould with special functional implication of three complement-related fragments (CaC1q1, CaC1q2, and Cac3)," Fish & Shellfish Immunoogy 32(6): 1106-16 (2012).

Yuan et al., "Cloning and sequence analysis of metallothionein gene in Hyriopsis cumingii," Dongwuxue Zazhi 44(5): 98-104 (2009) (English Abstract Only).

\* cited by examiner

COMPOSITIONS AND METHODS FOR THE TREATMENT OF CAST NEPHROPATHY AND RELATED CONDITIONS

RELATED APPLICATIONS

This application claims priority to U.S. Provisional Application No. 62/380,068 filed Aug. 26, 2016, the entire contents of which are incorporate herein by reference.

SEQUENCE LISTING

The instant application contains a Sequence Listing which has been submitted electronically in ASCII format and is hereby incorporated by reference in its entirety. Said ASCII copy, created on Dec. 21, 2016, is named 119562-03502_SL.txt and is 20,665 bytes in size.

BACKGROUND

Multiple myeloma is a neoplastic disorder characterized by a clonal proliferation of malignant plasma cells, which produce monoclonal immunoglobulins (i.e., antibodies). Acute kidney injury (AKI) is a well-known complication of multiple myeloma with high tumor burden and high amounts of light chains (which are fragments of immunoglobulins) in the urine. AKI affects up to 50% of patients with multiple myeloma, and has important consequences: it exposes patients to the risk of permanent kidney damage (including end stage kidney failure), is associated with a decrease in overall survival, and impacts the treatment of the underlying myeloma.

In the vast majority of cases, AKI is due to myeloma cast nephropathy that results from the precipitation of complexes (called myeloma casts) formed by light chains and uromodulin (a protein normally present in urine) in the distal part of the nephron. See Leung et al., Adv Chronic Kidney Dis, 21: 36-47. These casts obstruct the nephrons, leading to AKI and induce an inflammatory reaction that leads to fibrosis and irreversible chronic kidney damage. The events leading to cast formation have been dissected. See Huang, et al., J Clin Invest, 92: 2975-83, 1993; Huang, et al., J Clin Invest, 99: 732-6, 1997. In particular, different light chains were found to bind to the same peptidic segment of uromodulin (later identified as D8C) and interacted with uromodulin through their CDJ3 (for complementarity-determining region 3). This finding led to the indentation of a CDJ3 sequence derived peptide that blocked the interaction between monoclonal light chains and uromodulin, and inhibited cast formation in vivo. See e.g., Ying, et al., Am J Pathol, 158: 1859-66, 2012.

Recognizing this result, peptides that inhibit the binding of light chains to uromodulin represent are an attractive targets for combating myeloma cast nephropathy and related conditions.

SUMMARY OF THE INVENTION

Provided herein are peptides and compositions thereof which are effective binding inhibitors of light chains to uromodulin. (See e.g., Table 3). Such peptides include those of Formula SEQ ID No. 1:

$$J^1CysX^1X^2X^3X^4X^5X^6ProX^7ThrCysJ2^3(J^4)_s(J^5)_t; \quad \text{(SEQ ID No. 1)}$$

or a pharmaceutically acceptable salt thereof, wherein each of $X^1$, $X^2$, $X^3$, $X^4$, $X^5$, $X^6$, $X^7$, $J^1$, $J^2$ $J^3$, $J^4$, $J^5$, s, and t are as defined and described herein.

Also provided are methods of treating myeloma cast nephropathy in e.g., patient populations with severe renal impairment, comprising administering one or more of the peptides or compositions described herein.

DETAILED DESCRIPTION OF CERTAIN EMBODIMENTS

1. General Description of Peptides

Figure 1:
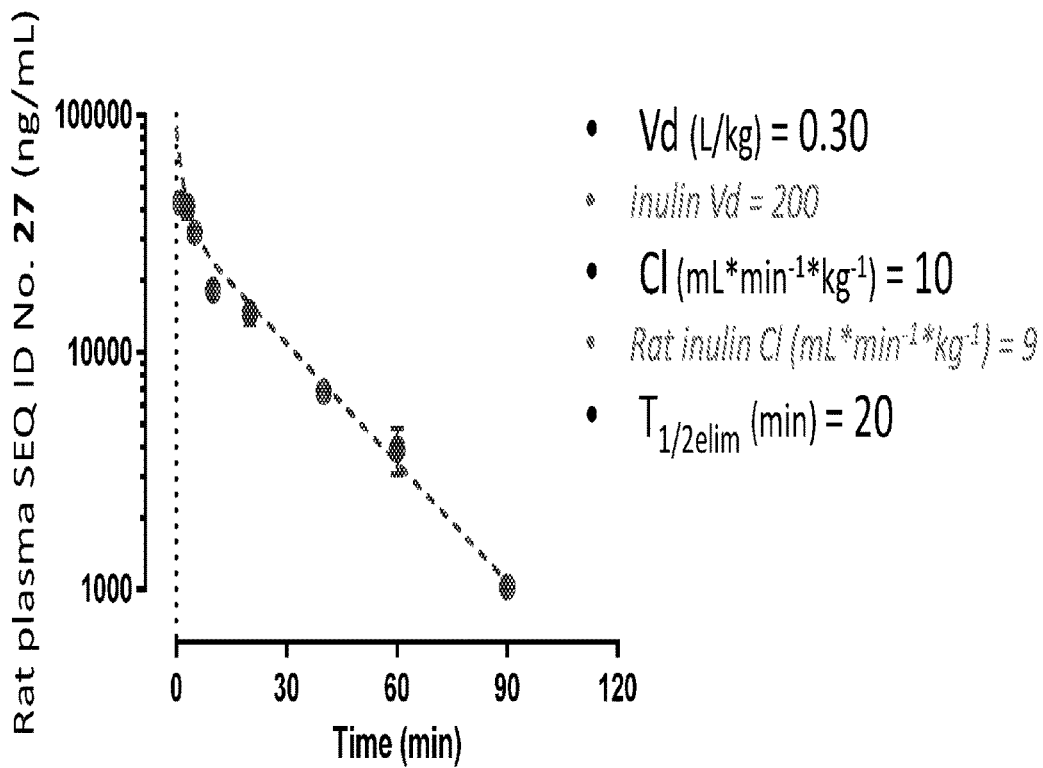
FIG. 1 illustrates the plasma pharmacokinetics following intravenous bolus injection of a peptide of Formula SEQ ID No. 1 in rat.

In one aspect, provided herein are peptides of Formula SEQ ID No. 1:

$$J^1CysX^1X^2X^3X^4X^5X^6ProX^7ThrCysJ2^3(J^4)_s(J^5)_t; \quad \text{(SEQ ID No. 1)}$$

or a pharmaceutically acceptable salt thereof, wherein
$J^1$ is Aha or Arg;
$X^1$ to $X^7$ are each independently a natural or non-natural amino acid;
s, and t are each independently 0 or 1;
$J^2$ and $J^3$ are each independently Lys or Arg;
$J^4$, if present is Lys or Arg; and
$J^5$, if present is Lys or Arg.

2. Peptides and Definitions

"Amino acid" refers to an organic compound containing an amine ($-NH_2$) and a carboxylic acid ($-COOH$) functional group, usually along with a side-chain specific to each amino acid. Amino acids can be classified according to the core structural functional groups' locations as alpha- ($\alpha$-), beta- ($\beta$-), gamma- ($\gamma$-) or delta- ($\delta$-) amino acids; other categories relate to polarity, pH level, and side-chain group type (aliphatic, acyclic, aromatic, containing hydroxyl or sulfur, etc.). In one embodiment, amino acid includes "Natural amino acid" is used interchangeably with proteinogenic amino acid and refers to the 20 standard amino acids encoded by the universal genetic code along with selenocysteine and pyrolysine. The 20 standard amino acids encoded by the universal genetic code include glycine, alanine, valine, leucine, isoleucine, proline, phenylalanine, tyrosine, tryptophan, serine, threonine, cysteine, methionine, asparagine, glutamine, aspartate, glutamate, lysine, arginine, and histidine. Unless otherwise specified, when a natural amino acid is defined without indicating the stereochemistry it will be understood that the defined amino acid is present as the L-enantiomer. Thus, when used as part of a formula, the letter A or Ala means L-alanine.

The full name of a natural amino acid and its corresponding three-letter or one-letter code are used interchangeably. For example, glycine is interchangeable with three letter abbreviation Gly or the one letter abbreviation G; alanine is interchangeable with three letter abbreviation Ala or the one letter abbreviation A, valine is interchangeable with three letter abbreviation Val or the one letter abbreviation V, leucine is interchangeable with three letter abbreviation Leu or the one letter abbreviation L, isoleucine is interchangeable with three letter abbreviation Ile or the one letter abbreviation I, proline is interchangeable with three letter abbreviation Pro or the one letter abbreviation P, phenylalanine is interchangeable with three letter abbreviation Phe or the one letter abbreviation F, tyrosine is interchangeable with three letter abbreviation Tyr or the one letter abbreviation Y, tryptophan is interchangeable with three letter abbreviation Trp or the one letter abbreviation W, serine is interchangeable with three letter abbreviation Ser or the one letter abbreviation S, threonine is interchangeable with three letter abbreviation Thr or the one letter abbreviation T, cysteine is interchangeable with three letter abbreviation Cys or the one letter abbreviation C, methionine is interchangeable with three letter abbreviation Met or the one letter abbreviation M, asparagine is interchangeable with three letter abbreviation Asn or the one letter abbreviation N, glutamine is interchangeable with three letter abbreviation Gln or the one letter abbreviation Q, aspartate is interchangeable with three letter abbreviation Asp or the one letter abbreviation D, glutamate is interchangeable with three letter abbreviation Glu or the one letter abbreviation E, lysine is interchangeable with three letter abbreviation Lys or the one letter abbreviation K, arginine is interchangeable with three letter abbreviation Arg or the one letter abbreviation R, histidine is interchangeable with three letter abbreviation His or the one letter abbreviation H, selenocysteine is interchangeable with three letter abbreviation Sec or the one letter abbreviation U, and pyrolysine is interchangeable with three letter abbreviation Pyl or the one letter abbreviation O. In one embodiment, the term "natural amino acid" or proteinogenic amino acid refers only to the 20 standard amino acids encoded by the universal genetic code, i.e., G, A, V, L, I, P, F, Y, W, S, T, C, M, N, Q, D, E, K, R, and H.

"Non-natural amino acid" refers to a non-proteinogenic amino acid that is not found in proteins (e.g., carnitine, gamma-aminobutyric acid, and D-forms of natural amino acids except glycine) or not produced directly and in isolation by standard cellular machinery (e.g., hydroxyproline and selenomethionine). Other examples include, but are not limited to, β-amino acids (β3 and β2), homo-amino acids, alanine derivatives, alicyclic amino acids, arginine derivatives, asparagine derivatives, aspartic acid derivatives, cysteine derivatives, 2,4-diaminobutyric acid, glycine derivatives, isoleucine derivatives, leucine derivatives, lysine derivatives (such as 6-aminohexanoic acid abbreviated herein as Aha), methionine derivatives, norleucine (nL) and norleucine derivatives, phenylalanine derivatives, phenylglycine derivatives, proline and pyruvic acid derivatives, pyroglutamine derivatives, serine derivatives, threonine derivatives, tryptophan derivatives, norvaline derivatives, 2,3-diaminopropionic acid, ornithine derivatives, valine derivatives, linear core amino acids, and N-methyl amino acids. In one embodiment, the term "non-natural amino acid" refers only to D-forms of the 20 standard amino acids encoded by the universal genetic code. These forms include D-Ala, D-Val, D-Leu, D-Ile, D-Pro, D-Phe, D-Tyr, D-Trp, D-Ser, D-Thr, D-Cys, D-Met, D-Asn, D-Gln, D-Asp, D-Glu, D-Lys, D-Arg, and D-His.

The abbreviation "oxC" means a compound of the structure

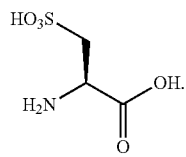

The abbreviation "Pen" means a compound of the structure

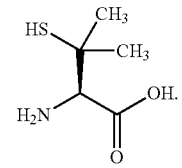

A "D-amino acid" or D-form of an amino acid means that the indicated amino acid is present as the D-enantiomer. Shorthand notation for the D-enantiomer of an amino acid can be represented by an asterisk (*). For example, I* or I*le, wherein * represents a D-amino acid, refers to the D-enantiomer of Ile (isoleucine).

The peptides described herein may be present in the form of pharmaceutically acceptable salts. Pharmaceutically acceptable salts are art-recognized and include e.g., relatively non-toxic inorganic and organic acid addition salts, or inorganic or organic base addition salts that are suitable for human consumption. Examples of such salts include, but are not limited to, sodium, potassium, calcium, magnesium, acetate, benzoate, bicarbonate, carbonate, citrate, dihydrochloride, gluconate, glutamate, hydrochloride, and tartrate.

The term "pharmaceutically acceptable carrier" refers to a non-toxic carrier, adjuvant, or vehicle that does not adversely affect the pharmacological activity of the peptide with which it is formulated, and which is also safe for human use. Pharmaceutically acceptable carriers that may be used include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, dicalcium phosphate, potassium hydrogen phosphate, sodium chloride, zinc salts, colloidal silica, magnesium trisilicate, polyvinyl pyrrolidone, polyvinylpyrrolidone-vinyl acetate, cellulose-based substances (e.g., microcrystalline cellulose, hydroxypropyl methylcellulose, hydroxypropyl methylcellulose acetate succinate, hydroxypropyl methylcellulose Phthalate), starch, lactose monohydrate, mannitol, trehalose sodium lauryl sulfate, and crosscarmellose sodium, polyethylene glycol, sodium carboxymethylcellulose, polyacrylates, polymethacrylate, waxes, polyethylene-polyoxypropylene-block polymers, polyethylene glycol and wool fat.

The terms "subject" and "patient" may be used interchangeably, and mean a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The terms "treatment," "treat," and "treating" refer to reversing, alleviating, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

An "effective amount" or "therapeutically effective amount" is a quantity sufficient to achieve a desired therapeutic and/or prophylactic effect, for example, an amount which results in the prevention of or a decrease in the symptoms associated with a condition that is being treated, e.g., the conditions described herein.

3. Description of Exemplary Peptides

In a first embodiment, provided herein are peptides of the Formula SEQ ID No. 1:

$$J^1CysX^1X^2X^3X^4X^5X^6ProX^7ThrCysJ^2J^3(J^4)_s(J^5)_r;$$ (SEQ ID No. 1)

or a pharmaceutically acceptable salt thereof, wherein the variables are as described above.

In a second embodiment, $X^6$ in the peptide of Formula SEQ ID No. 1 is not Glu, Thr, Asn, or Asp; and $X^7$ is not Glu or Asp, wherein the remaining variables in SEQ ID No. 1 are as described above.

In a third embodiment, $X^1$ in the peptide of Formula SEQ ID No. 1 is selected from Arg, Lys, His, Pro, Cys, Thr, Ser, Gln, Glu, Leu, Ile, Met, Ala, Val, Gly, n-Leu, Met, Asp, and Ile, wherein the remaining variables in SEQ ID No. 1 are as described above for SEQ ID No. 1 or the second embodiment. Alternatively, $X^1$ in the peptide of Formula SEQ ID No. 1 is selected from Arg, Gln, Glu, Leu, n-Leu, Met, Asp, and Ile, wherein the remaining variables in SEQ ID No. 1 are as described above for SEQ ID No. 1 or the second embodiment. In another alternative, $X^1$ in the peptide of Formula SEQ ID No. 1 is selected from Gln, Leu, and n-Leu, wherein the remaining variables in SEQ ID No. 1 are as described above for SEQ ID No. 1 or the second embodiment.

In a forth embodiment, $X^2$ in the peptide of Formula SEQ ID No. 1 is selected from a natural amino acid, wherein the remaining variables in SEQ ID No. 1 are as described above for SEQ ID No. 1 or the second or third embodiment. Alternatively, $X^2$ in the peptide of Formula SEQ ID No. 1 is selected from Ser, Thr, Cys, Met, Asn, Lys, Gln, His, Arg, Glu, and Asp, wherein the remaining variables in SEQ ID No. 1 are as described above for SEQ ID No. 1 or the second or third embodiment. In another alternative, $X^2$ in the peptide of Formula SEQ ID No. 1 is selected from Ser, Gln, His, Arg, Glu, and Asp, wherein the remaining variables in SEQ ID No. 1 are as described above for SEQ ID No. 1 or the second or third embodiment. In yet another alternative, $X^2$ in the peptide of Formula SEQ ID No. 1 is selected from Gln and His, wherein the remaining variables in SEQ ID No. 1 are as described above for SEQ ID No. 1 or the second or third embodiment.

In a fifth embodiment, $X^3$ in the peptide of Formula SEQ ID No. 1 is selected from a natural amino acid, wherein the remaining variables in SEQ ID No. 1 are as described above for SEQ ID No. 1 or the second, third, or forth embodiment. Alternatively, $X^3$ in the peptide of Formula SEQ ID No. 1 is selected from Tyr, Trp, Phe, Ser, Thr, Cys, Met, Asn, Ala, Lys, His, Glu, Arg, and Asp, wherein the remaining variables in SEQ ID No. 1 are as described above for SEQ ID No. 1 or the second, third, or forth embodiment. In another alternative, $X^3$ in the peptide of Formula SEQ ID No. 1 is selected from Tyr, Ser, Ala, Glu, Arg, and Asp, wherein the remaining variables in SEQ ID No. 1 are as described above for SEQ ID No. 1 or the second, third, or forth embodiment. In yet another alternative, $X^3$ is selected from Tyr, Ser, Arg, and Asp, wherein the remaining variables in SEQ ID No. 1 are as described above for SEQ ID No. 1 or the second, third, or forth embodiment.

In a sixth embodiment, $X^4$ in the peptide of Formula SEQ ID No. 1 is selected from a natural amino acid, wherein the remaining variables in SEQ ID No. 1 are as described above for SEQ ID No. 1 or the second, third, fourth, or fifth embodiment. Alternatively, $X^4$ in the peptide of Formula SEQ ID No. 1 is selected from Gly, Ala, Val, Leu, Ile, Pro, Phe, Tyr, Trp, Asp, Glu, Lys, Arg, and His, wherein the remaining variables in SEQ ID No. 1 are as described above for SEQ ID No. 1 or the second, third, fourth, or fifth embodiment. In another alternative, $X^4$ in the peptide of Formula SEQ ID No. 1 is selected from Leu, Asp, Gly, Tyr, Glu, and Arg, wherein the remaining variables in SEQ ID No. 1 are as described above for SEQ ID No. 1 or the second, third, fourth, or fifth embodiment. In yet another alternative $X^4$ in the peptide of Formula SEQ ID No. 1 is selected from Leu, Asp, Tyr, and Arg, wherein the remaining variables in SEQ ID No. 1 are as described above for SEQ ID No. 1 or the second, third, fourth, or fifth embodiment.

In a seventh embodiment, $X^5$ in the peptide of Formula SEQ ID No. 1 is selected from a natural amino acid, wherein the remaining variables in SEQ ID No. 1 are as described above for SEQ ID No. 1 or the second, third, fourth, fifth, or sixth embodiment. Alternatively, $X^5$ in the peptide of Formula SEQ ID No. 1 is selected from Ser, Thr, Cys, Met, Asn, Gln, Asp, Glu, Lys, Arg, and His, wherein the remaining variables in SEQ ID No. 1 are as described above for SEQ ID No. 1 or the second, third, fourth, fifth, or sixth embodiment. In another alternative, $X^5$ in the peptide of Formula SEQ ID No. 1 is selected from Tyr, Ser, Arg, Glu, and Asp, wherein the remaining variables in SEQ ID No. 1 are as described above for SEQ ID No. 1 or the second, third, fourth, fifth, or sixth embodiment.

In an eighth embodiment, $X^6$ in the peptide of Formula SEQ ID No. 1 is selected from Gly, Ala, Val, Leu, Ile, Pro, Phe, Tyr, Trp, Ser, Cys, Met, Gln, Lys, Arg, and His, wherein the remaining variables in SEQ ID No. 1 are as described above for SEQ ID No. 1 or the second, third, fourth, fifth, sixth, or seventh embodiment. Alternatively, $X^6$ in the peptide of Formula SEQ ID No. 1 is selected from Ile, Leu, Pro, Val, Ala, Gly, His, Lys, and Arg, wherein the remaining variables in SEQ ID No. 1 are as described above for SEQ ID No. 1 or the second, third, fourth, fifth, sixth, or seventh embodiment. In another alternative, $X^6$ in the peptide of Formula SEQ ID No. 1 is selected from Ile, Leu, and Arg, wherein the remaining variables in SEQ ID No. 1 are as described above for SEQ ID No. 1 or the second, third, fourth, fifth, sixth, or seventh embodiment. In yet another alternative, $X^6$ in the peptide of Formula SEQ ID No. 1 is selected from Ile and Leu, wherein the remaining variables in SEQ ID No. 1 are as described above for SEQ ID No. 1 or the second, third, fourth, fifth, sixth, or seventh embodiment.

In a ninth embodiment, $X^7$ in the peptide of Formula SEQ ID No. 1 is selected from Gly, Ala, Val, Leu, Ile, Pro, Phe, Tyr, Trp, Ser, Thr, Cys, Met, Asn, Gln, Lys, Arg, and His, wherein the remaining variables in SEQ ID No. 1 are as described above for SEQ ID No. 1 or the second, third, fourth, fifth, sixth, seventh, or eighth embodiment. Alternatively, $X^7$ in the peptide of Formula SEQ ID No. 1 is selected from Tyr, Phe, His, Lys, Arg, and Trp, wherein the remaining variables in SEQ ID No. 1 are as described above for SEQ ID No. 1 or the second, third, fourth, fifth, sixth, seventh, or eighth embodiment. In another alternative, $X^7$ in the peptide of Formula SEQ ID No. 1 is selected from Tyr, Arg, and Trp, wherein the remaining variables in SEQ ID No. 1 are as described above for SEQ ID No. 1 or the second, third, fourth, fifth, sixth, seventh, or eighth embodiment. In yet another alternative, $X^7$ in the peptide of Formula SEQ ID No. 1 is Tyr, wherein the remaining variables in SEQ ID No. 1 are as described above for SEQ ID No. 1 or the second, third, fourth, fifth, sixth, seventh, or eighth embodiment.

In a tenth embodiment, s and t are each 0 in the peptide of Formula SEQ ID No. 1, wherein the remaining variables in SEQ ID No. 1 are as described above for SEQ ID No. 1 or the second, third, fourth, fifth, sixth, seventh, eighth, or ninth embodiment.

In an eleventh embodiment, s and t are each 1 in the peptide of Formula SEQ ID No. 1, wherein the remaining variables in SEQ ID No. 1 are as described above for SEQ ID No. 1 or the second, third, fourth, fifth, sixth, seventh, eighth, ninth, or tenth embodiment.

In a thirteenth embodiment, $J^1$ in the peptide of Formula SEQ ID No. 1 is Aha, wherein the remaining variables in SEQ ID No. 1 are as described above for SEQ ID No. 1 or the second, third, fourth, fifth, sixth, seventh, eighth, ninth, tenth, or eleventh embodiment.

Specific examples of the disclosed peptides are provided in Table 1 and Table 2 below as well as in the EXEMPLIFICATION sections. Pharmaceutically acceptable salts as well as the neutral forms of these peptides are included in the present disclosure.

TABLE 1

| SEQ ID No. | Sequence |
|---|---|
| 11 | AhaCQQSYSIPWTCKK |
| 12 | AhaCQQSYSIPYTCKK |
| 13 | AhaCQQYDSLPLTCKK |
| 14 | AhaCQQYSYLPITCK*K* |
| 15 | AhaCQQYSTAPWTCKK |
| 16 | AhaCQQYYSAPPTCKK |
| 17 | AhaCQQYKNYPWTCKK |
| 18 | AhaCQHYDYLPITCK*K* |
| 20 | AhaCQQSYSIPWTCK*K* |
| 21 | AhaCQQSYSIPYTCK*K* |
| 22 | AhaCQQ*SYSIPWTCK*K* |
| 23 | AhaCQQS*YSIPWTCK*K* |
| 24 | AhaCQQSY*SIPWTCK*K* |
| 25 | AhaCQQ*SYSIPYTCK*K* |
| 26 | AhaCQQS*YSIPYTCK*K* |
| 27 | AhaCQQSY*SIPYTCK*K* |
| 28 | AhaCEQSYSIPYTCKK |
| 29 | AhaCQESYSIPYTCKK |
| 30 | AhaCQQEYSIPYTCKK |
| 31 | AhaCQQSESIPYTCKK |
| 32 | AhaCQQSYEIPYTCKK |
| 33 | AhaCQQSYSEPYTCKK |
| 34 | AhaCQQSYSIEYTCKK |
| 35 | AhaCQQSYSIPETCKK |
| 36 | AhaCQQSYSIPYECKK |
| 37 | AhaCRQSYSIPYTCKK |
| 38 | AhaCQRSYSIPYTCKK |
| 39 | AhaCQQRYSIPYTCKK |
| 40 | AhaCQQSRSIPYTCKK |
| 41 | AhaCQQSYRIPYTCKK |
| 42 | AhaCQQSYSRPYTCKK |
| 43 | AhaCQQSYSIRYTCKK |
| 44 | AhaCQQSYSIPRTCKK |
| 45 | AhaCQQSYSIPYRCKK |
| 46 | AhaCQQSY*SIPYTCK*K*K* |
| 50 | AhaCQQYSYLPITCK*K* |
| 51 | AhaCQQYSYLPITCR*R* |

TABLE 1-continued

| SEQ ID No. | Sequence |
|---|---|
| 52 | AhaCQQSYLPITCK*K* |
| 53 | AhaCQQYSLPITCK*K* |
| 54 | AhaCQQYDLPITCK*K* |
| 55 | AhaCQQSYSIPYTCR*R* |

TABLE 2

| SEQ ID No. | Sequence |
|---|---|
| 2 | AhaCAAWDDSLNGPVCKK |
| 3 | AhaCnLQALRTPLYTCKK |
| 4 | AhaCLSADSSGSYLYVCKK |
| 5 | AhaCQVWDNSVGVCKK |
| 6 | AhaCQSYDNTLSGSYVCKK |
| 7 | AhaCQSYDNTLSGSLCKK |
| 8 | AhaCQSYDARNV |
| 9 | AhaCQSYDHNNQ |
| 10 | AhaCQSYDSTNEGVCKK |
| 19 | AhaCQHYGSSALTCKK |
| 47 | K*K*CQQSY*SIPYTCK*K* |
| 48 | AhaPenQQSY*SIPYTPenK*K* |
| 49 | oxCCQQSY*SIPYTCK*K* |

4. Uses, Formulation, and Administration

In certain embodiments, the present disclosure provides a method of treating a subject (e.g., a human) suffering from myeloma cast nephropathy, comprising administering to the subject a therapeutically effective amount of a peptide of Formula SEQ ID No. 1, or a pharmaceutically acceptable salt thereof. In certain embodiments, the amount of peptide of SEQ ID No. 1 is such that it is an effective binding inhibitor of light chains to uromodulin. In certain embodiments, a provided composition is formulated for administration to a subject in need of such composition.

Pharmaceutically acceptable compositions are included and can be administered to humans and other animals by other methods such as e.g., orally, rectally, parenterally, intracisternally, intraperitoneally, topically (as by powders, creams, ointments, or drops), bucally, as an oral or nasal spray, or the like. In certain embodiments, the disclosed peptides may be administered parenterally (e.g., intravenous).

In certain embodiments, the present disclosure also provides a method of treating a subject (e.g., a human) suffering from myeloma cast nephropathy, comprising administering to the subject a therapeutically effective amount of composition comprising a peptide of Formula SEQ ID No. 1, or a pharmaceutically acceptable salt thereof; and a pharmaceutically acceptable carrier. adjuvant, or vehicle. In certain embodiments, the amount of peptide of SEQ ID No. 1 in a provided composition is such that it is an effective binding inhibitor of light chains to uromodulin.

It will be understood that a specific dosage for any particular subject will depend upon a variety of factors, including age, body weight, general health, sex, diet, time of administration, rate of excretion, drug combination, the judgment of the treating physician, and the severity of the particular disease being treated. The amount of a provided peptide in the composition will also depend upon the particular peptide in the composition.

The amount of provided peptides that may be combined with carrier materials to produce a composition in a single dosage form will vary depending upon the patient to be treated and the particular mode of administration.

EXEMPLIFICATION

Standard solid phase techniques were employed to synthesize the disclosed peptides. Fmoc (fluorenylmethyloxycarbonyl) chemistry occurred on PEG-base Rink Amide resin, 0.45 mmol/g loading. Side-chain protection of Fmoc amino acid included t-Bu (t-butyl) on Asp, Ser, Tyr and D-Tyr; Trt (trityl) on Asn and Cys; Boc (tert-butyloxycarbonyl) on Lys; Pbf (2,2,4,6,7-pentamethyldihydrobenzofurane) on Arg, Fmoc on K* (i.e., Fmoc-Lys(Fmoc)-OH was used to coupled to the resin).

General Procedure

1. Fmoc Deprotection

Fmoc deprotection was performed using 20% piperidine in DMF (dimethylformamide) or 20% piperidine/0.1% 6-Cl HOBt (Hydroxybenzotriazole) in DMF, 5 min+20 min for each deprotection.

2. Coupling of Fmoc Amino Acids

Acylations were carried out using 3-fold Fmoc amino acids activated with DIC (3 eq.) (N,N'-Diisopropylcarbodiimide) in the presence of 6-Cl-HOBt (3 eq.). Each coupling reaction took on average 1-3 h for completion. Kaiser test was used throughout for the in-process control of the coupling completion and the Fmoc deprotection. In the case that the Kaiser test was not satisfactory, re-couplings were done using DIC/6-Cl HOBt or HCTU (2-(6-Chloro-1H-benzotriazole-1-yl)-1,1,3,3-tetramethylaminium hexafluorophosphate)/OxymaPure.

3. Resin Cleavage and Peptide Recovery

Peptidyl resin was extensively washed with DCM (dichloromethane) and methanol to remove the trace of DMF and dried at RT overnight. Peptidyl resin was cleavaged with the mixture of TFA/TIS/EDT/H$_2$O (trifluoroacetic acid/triethylsilane/1,2-ethanedithiol/water) (92.5/2.5/2.5/2.5, v/v/v/v) for 2.5-3 h under nitrogen bubbling. Peptides were collected by precipitation in cold diethyl ether/Hexane (1/1, v/v).

4. Purification of Linear Peptide

Crude liner peptide was purified using Phenomenex Gemini C-18 prep column. 21.5 mm×250 mm. The peptide was then dried by lyophilization.

5. Disulfide Bridge Formation

Purified linear peptide was dissolved in 0.1M ammonium bicarbonate (3-5 mg/ml), stand open to air for 2 days. Frequent HPLC testings were done to monitor the cyclization process. After cyclization, use TFA to adjust to acidic. isolated the product by lyophilization.

6. Cyclic Peptide Purification

Peptides were purified using the following conditions. Column: Phenomenex Gemini, 5 u, C18, 110 A, 250×21.2 mm Mobile phase A: 0.1% TFA in Acetonitrile/H$_2$O (50/50). Mobile phase B: 0.1% TFA/H$_2$O. Gradient: 0-100% A in 120 min Wavelength: 229 nm. Flow rate: 16-20 ml/min.

7. Isolation of Human Uromodulin

Uromodulin was precipitated from fresh urine from healthy donors using 0.58M NaCl. The precipitate was then washed with 0.58M NaCl and resuspended in water. The uromodulin was dialyzed extensively against water to remove salt and other contaminants (MWCo=50 KD). Samples were then stored at −20° C. without lyophilization. Good overall purity was seen by gel electrophoresis.

8. General Binding Assays

Enzyme-linked immunosorbant assays (ELISA) were performed on the disclosed peptides. Plates were coated with the following light chain clones overnight at 4° C.: 0.05 uM BER (subtype lambda, isolated from SP2/0 cells), 0.2 uM ROC (subtype kappa, isolated from CHO cells), and 0.3 uM BEN (subtype lambda, isolated from CHO cells). The plates were washed and treated with bovine serum albumin (BSA) overnight at 4° C. For peptide plates, 10 nM biotin-uromodulin was mixed with peptide overnight at 4° C. Plates were then washed and results were revealed using streptaviding-HRP (horseradish peroxidase) and 3,3',5,5'-tetramethylbenzidine (TMB). Results are shown in Table 3.

TABLE 3

| SEQ ID No. | Sequence | Binding Inhibition (IC$_{50}$ uM) | | |
|---|---|---|---|---|
| | | BER | BEN | ROC |
| 2 | AhaCAAWDDSLNGPVCKK | 500 | 500 | 500 |
| 3 | AhaCnLQALRTPLYTCKK | 16.0 | 12.0 | 14.9 |
| 4 | AhaCLSADSSGSYLYVCKK | 500 | 66 | 500 |
| 5 | AhaCQVWDNSVGVCKK | 500 | >120 | 18.5 |
| 6 | AhaCQSYDNTLSGSYVCKK | >120 | 19 | >120 |
| 7 | AhaCQSYDNTLSGSLCKK | 500 | 500 | 500 |
| 8 | AhaCQSYDARNV | 500 | 58.2 | 500 |
| 9 | AhaCQSYDHNNQ | 500 | 26.7 | 500 |
| 10 | AhaCQSYDSTNEGVCKK | 500 | 500 | 500 |
| 11 | AhaCQQSYSIPWTCKK | 34.4 | 3.2 | 20.8 |
| 12 | AhaCQQSYSIPYTCKK | 22.9 | 2.5 | 27.3 |
| 13 | AhaCQQYDSLPLTCKK | 21.3 | 3.3 | 31.9 |
| 14 | AhaCQQYSYLPITCK*K* | 17.3 | 2.8 | 20.9 |
| 15 | AhaCQQYSTAPWTCKK | 500 | 16.7 | 500 |
| 16 | AhaCQQYYSAPPTCKK | 500 | 14.3 | >120 |
| 17 | AhaCQQYKNYPWTCKK | 500 | 7.3 | >120 |
| 18 | AhaCQHYDYLPITCK*K* | 14.8 | 0.9 | 13.7 |
| 19 | AhaCQHYGSSALTCKK | 52 | 3.3 | 16.4 |
| 20 | AhaCQQSYSIPWTCK*K* | 60.1 | 2.6 | nt |
| 21 | AhaCQQSYSIPYTCK*K* | 49.8 | nt | 75.5 |
| 22 | AhaCQQ*SYSIPWTCK*K* | 96.9 | nt | nt |
| 23 | AhaCQQS*YSIPWTCK*K* | 54.1 | nt | nt |
| 24 | AhaCQQSY*SIPWTCK*K* | 67.8 | nt | nt |
| 25 | AhaCQQ*SYSIPYTCK*K* | 35.9 | nt | 22.0 |
| 26 | AhaCQQS*YSIPYTCK*K* | 30.1 | nt | 27.5 |
| 27 | AhaCQQSY*SIPYTCK*K* | 27.1 | 2.8 | 26.5 |
| 28 | AhaCEQSYSIPYTCKK | 24.9 | nt | 25.2 |
| 29 | AhaCQESYSIPYTCKK | 26.3 | nt | 25.5 |
| 30 | AhaCQQEYSIPYTCKK | 26.5 | nt | 25.9 |
| 31 | AhaCQQSESIPYTCKK | 25.9 | nt | 24.1 |
| 32 | AhaCQQSYEIPYTCKK | Nt | nt | 28 |
| 33 | AhaCQQSYSEPYTCKK | >120 | nt | >120 |
| 34 | AhaCQQSYSIEYTCKK | >500 | nt | >120 |
| 35 | AhaCQQSYSIPETCKK | >120 | nt | >120 |
| 36 | AhaCQQSYSIPYECKK | >120 | nt | >500 |
| 37 | AhaCRQSYSIPYTCKK | 49.8 | nt | 27.9 |
| 38 | AhaCQRSYSIPYTCKK | 55 | nt | 26.4 |
| 39 | AhaCQQRYSIPYTCKK | 20.7 | nt | 22.1 |
| 40 | AhaCQQSRSIPYTCKK | 23.5 | nt | 26.2 |
| 41 | AhaCQQSYRIPYTCKK | 20.9 | nt | 21.6 |
| 42 | AhaCQQSYSRPYTCKK | 27.8 | nt | 29.5 |
| 43 | AhaCQQSYSIRYTCKK | >500 | nt | >120 |
| 44 | AhaCQQSYSIPRTCKK | 24.9 | nt | 25 |
| 45 | AhaCQQSYSIPYRCKK | >500 | nt | >500 |
| 46 | AhaCQQSY*SIPYTCK*K*K*K* | 23.4 | nt | 35.0 |
| 47 | K*K*CQQSY*SIPYTCK*K* | 32.3 | nt | 33.5 |
| 48 | AhaPenQQSY*SIPYTPenK*K* | 120.0 | nt | 120.0 |
| 49 | oxCCQQSY*SIPYTCK*K* | 43.3 | nt | 41.2 |
| 50 | AhaCQQYSYLPITCK*K* | 17.3 | nt | nt |
| 51 | AhaCQQYSYLPITCR*R* | 13.6 | nt | nt |
| 52 | AhaCQQSYLPITCK*K* | 69.0 | nt | nt |
| 53 | AhaCQQYSLPITCK*K* | 120.0 | nt | nt |
| 54 | AhaCQQYDLPITCK*K* | 120.0 | nt | nt |
| 56 | AhaCnLQALRTPLYTCR*R* | 10.6 | 2.0 | 18.1 | nt = not tested

8. Ex Vivo Conditions

Binding inhibition, stability, and solubility data was obtained for peptides of the Formula SEQ ID No. 1. These results are shown in Table 4. MLC$_{90}$ represents the lowest IC$_{50}$ at which uromodulin binding to 90% of the light chains tested was inhibited. KBB is kidney br

TABLE 4

| SEQ ID No. | Binding Inhibition MLC$_{90}$ | Stability | | | Solubility (saline, mg/mL) |
| --- | --- | --- | --- | --- | --- |
| | | Plasma$_{50\%}$ | KBB$_{50\%}$ | Urine$_{80\%}$ | |
| 11 | nt | <5 min | 5 min | >2 hrs | ≥100 |
| 27 | 27.1 | >120 min | >60 min | >2 hrs | ≥100 |

9. Pharmacokinetic Evaluations

Figure 2:
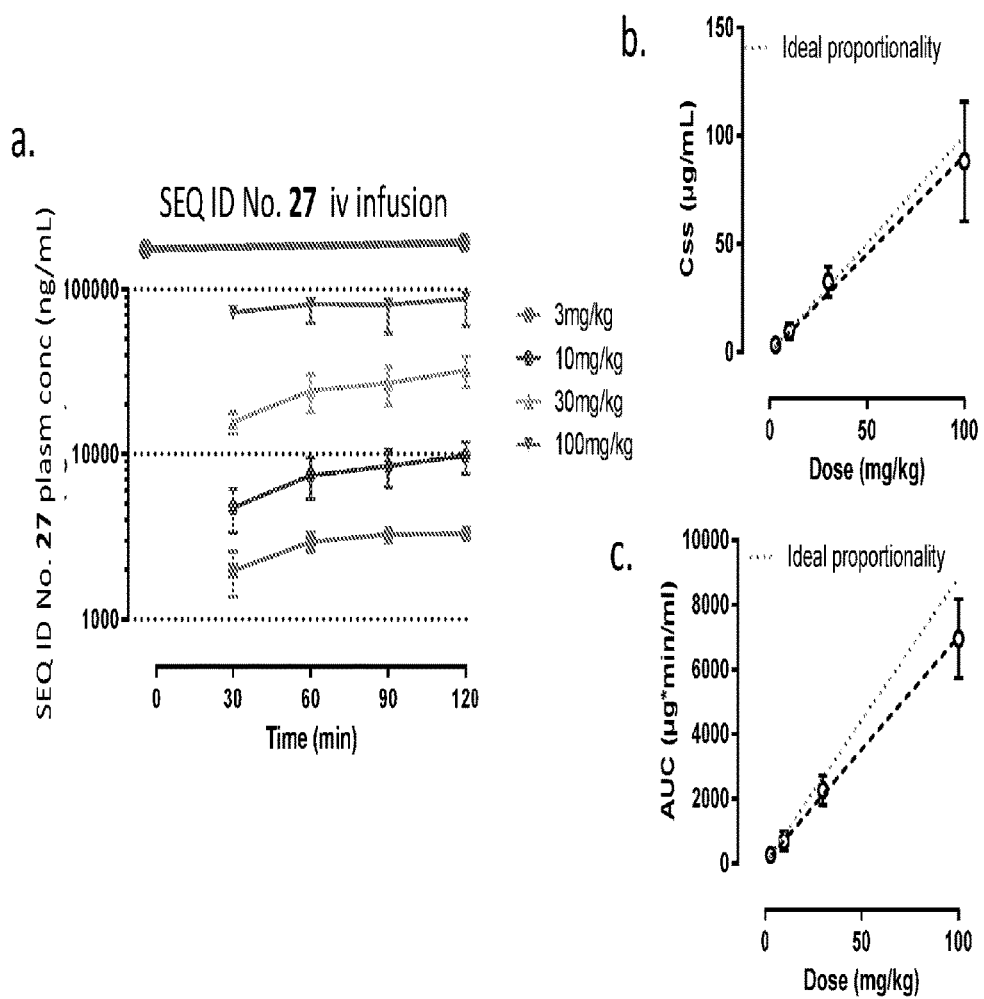
FIG. 2 illustrates the plasma pharmacokinetics following 2 hour intravenous infusion of a peptide of Formula SEQ ID No. 1 in rat.
Figure 3:
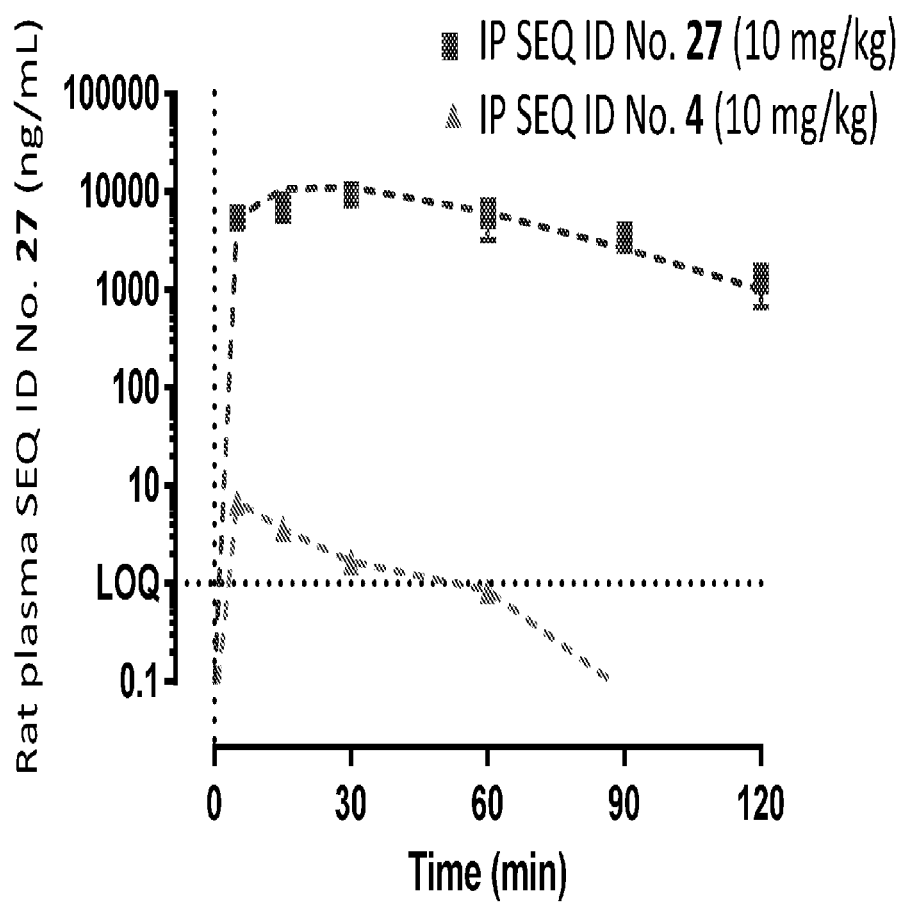
FIG. 3 compares the plasma pharmacokinetics of two peptides of Formula SEQ ID No. 1 after intraperitoneal injection in rat, where a.) shows a plot of peptide vs time at various concentrations; b.) shows a plot of steady state concentration (Css) as a function of. dose; and c.) shows a plot of the Area Under the Cure (AUC) as a function of dose.

The plasma pharmacokinetics of SEQ ID No. 27 was evaluated following intravenous (IV) bolus injection (FIG. 1) and 2 hour IV infusion (FIG. 2) in rats. Similarly, FIG. 3 plasma pharmacokinetics of SEQ ID No. 27 following intraperitoneal injection of SEQ ID No. 27 when compared with SEQ ID No. 4 in rat. This data establishes that peptides having SEQ ID No. 1, in particular SEQ ID No. 27, has high efficacy and very good dose-exposure proportionally over a broad range of doses.

Figure 4:
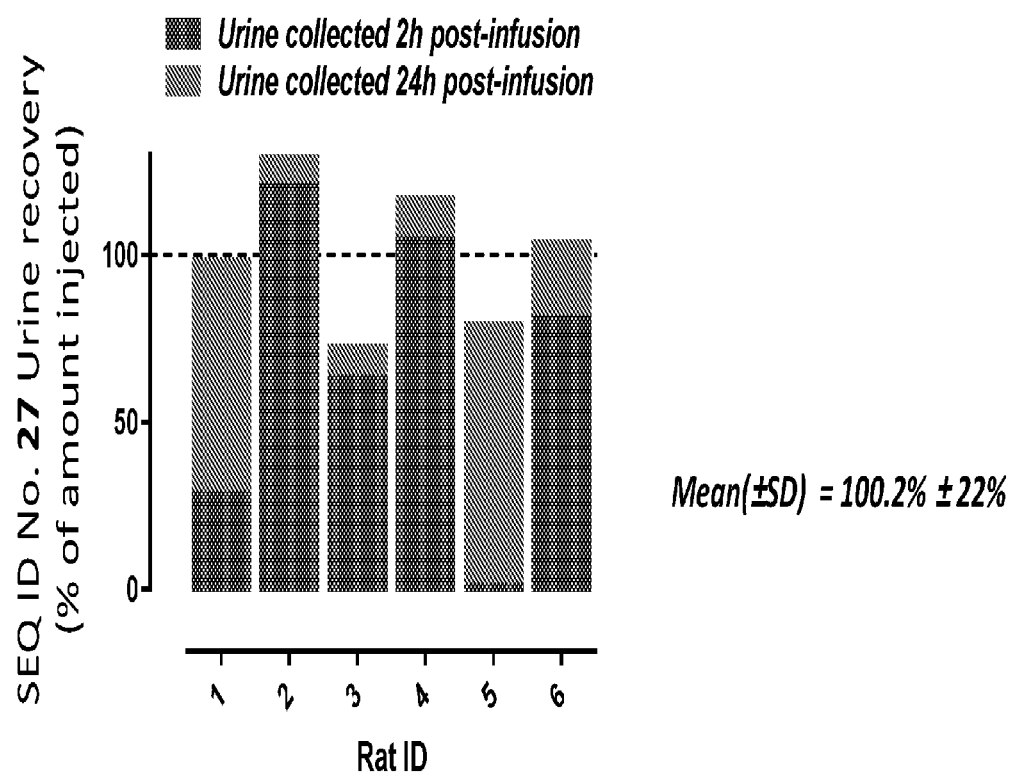
FIG. 4 illustrates the urine recovery of a peptide of Formula SEQ ID No. 1.

Surprisingly, and perhaps most notably, the clearance rate of SEQ ID No. 27 was essentially equal to the glomerular filtration rate, e.g., after infusion of 10 mg/kg of SEQ ID No. 27 for 2 hours to 6 rats, the percentage of intact peptide recovered in the urine was 100%±22% (mean±SD). See FIG. 4.

It will be appreciated that the scope of this invention is to be defined by the appended claims rather than by the specific embodiments that have been represented by way of example. The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A peptide of the Formula:

AhaCQQSY*SIPYTCK*K*;

or a pharmaceutically acceptable salt thereof.

2. A pharmaceutical composition comprising the peptide of claim 1, or a pharmaceutically acceptable salt thereof; and a pharmaceutically acceptable carrier.

3. A method of treating cast nephropathy in a subject in need thereof, comprising administering to the subject a therapeutically effective amount of the peptide of claim 1 peptide, or a pharmaceutically acceptable salt thereof.

* * * * *

SEQUENCE LISTING

```
<160> NUMBER OF SEQ ID NOS: 56

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha or Arg
<220> FEATURE:
<221> NAME/KEY: MOD_RES
<222> LOCATION: (3)..(8)
<223> OTHER INFORMATION: Any natural or non-natural amino acid
<220> FEATURE:
<221> NAME/KEY: MOD_RES
<222> LOCATION: (10)..(10)
<223> OTHER INFORMATION: Any natural or non-natural amino acid
<220> FEATURE:
<221> NAME/KEY: MOD_RES
<222> LOCATION: (13)..(14)
<223> OTHER INFORMATION: Lys or Arg
<220> FEATURE:
<221> NAME/KEY: MOD_RES
<222> LOCATION: (15)..(16)
<223> OTHER INFORMATION: Lys, Arg or not present
<220> FEATURE:
<223> OTHER INFORMATION: See specification as filed for detailed
      description of substitutions and preferred embodiments

<400> SEQUENCE: 1

Xaa Cys Xaa Xaa Xaa Xaa Xaa Xaa Pro Xaa Thr Cys Xaa Xaa Xaa Xaa
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 2
```

```
Xaa Cys Ala Ala Trp Asp Asp Ser Leu Asn Gly Pro Val Cys Lys Lys
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (3)..(3)
<223> OTHER INFORMATION: Norleucine

<400> SEQUENCE: 3

Xaa Cys Leu Gln Ala Leu Arg Thr Pro Leu Tyr Thr Cys Lys Lys
 1               5                  10                  15

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 4

Xaa Cys Leu Ser Ala Asp Ser Ser Gly Ser Tyr Leu Tyr Val Cys Lys
 1               5                  10                  15

Lys

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 5

Xaa Cys Gln Val Trp Asp Asn Ser Val Gly Val Cys Lys Lys
 1               5                  10

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 6

Xaa Cys Gln Ser Tyr Asp Asn Thr Leu Ser Gly Ser Tyr Val Cys Lys
```

```
1               5                   10                  15

Lys

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 7

Xaa Cys Gln Ser Tyr Asp Asn Thr Leu Ser Gly Ser Leu Cys Lys Lys
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 8

Xaa Cys Gln Ser Tyr Asp Ala Arg Asn Val
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 9

Xaa Cys Gln Ser Tyr Asp His Asn Asn Gln
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 10

Xaa Cys Gln Ser Tyr Asp Ser Thr Asn Glu Gly Val Cys Lys Lys
1               5                   10                  15

<210> SEQ ID NO 11
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 11

Xaa Cys Gln Gln Ser Tyr Ser Ile Pro Trp Thr Cys Lys Lys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 12

Xaa Cys Gln Gln Ser Tyr Ser Ile Pro Tyr Thr Cys Lys Lys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 13

Xaa Cys Gln Gln Tyr Asp Ser Leu Pro Leu Thr Cys Lys Lys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (13)..(14)
<223> OTHER INFORMATION: D-Lys

<400> SEQUENCE: 14

Xaa Cys Gln Gln Tyr Ser Tyr Leu Pro Ile Thr Cys Lys Lys
1               5                   10

<210> SEQ ID NO 15
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 15

Xaa Cys Gln Gln Tyr Ser Thr Ala Pro Trp Thr Cys Lys Lys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 16

Xaa Cys Gln Gln Tyr Tyr Ser Ala Pro Pro Thr Cys Lys Lys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 17

Xaa Cys Gln Gln Tyr Lys Asn Tyr Pro Trp Thr Cys Lys Lys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (13)..(14)
<223> OTHER INFORMATION: D-Lys

<400> SEQUENCE: 18

Xaa Cys Gln His Tyr Asp Tyr Leu Pro Ile Thr Cys Lys Lys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Aha

<400> SEQUENCE: 19

Xaa Cys Gln His Tyr Gly Ser Ser Ala Leu Thr Cys Lys Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (13)..(14)
<223> OTHER INFORMATION: D-Lys

<400> SEQUENCE: 20

Xaa Cys Gln Gln Ser Tyr Ser Ile Pro Trp Thr Cys Lys Lys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (13)..(14)
<223> OTHER INFORMATION: D-Lys

<400> SEQUENCE: 21

Xaa Cys Gln Gln Ser Tyr Ser Ile Pro Tyr Thr Cys Lys Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (4)..(4)
<223> OTHER INFORMATION: D-Gln
<220> FEATURE:
<221> NAME/KEY: MOD_RES
<222> LOCATION: (13)..(14)
<223> OTHER INFORMATION: D-Lys

<400> SEQUENCE: 22

Xaa Cys Gln Gln Ser Tyr Ser Ile Pro Trp Thr Cys Lys Lys
1               5                   10
```

```
<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (5)..(5)
<223> OTHER INFORMATION: D-Ser
<220> FEATURE:
<221> NAME/KEY: MOD_RES
<222> LOCATION: (13)..(14)
<223> OTHER INFORMATION: D-Lys

<400> SEQUENCE: 23

Xaa Cys Gln Gln Ser Tyr Ser Ile Pro Trp Thr Cys Lys Lys
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (6)..(6)
<223> OTHER INFORMATION: D-Tyr
<220> FEATURE:
<221> NAME/KEY: MOD_RES
<222> LOCATION: (13)..(14)
<223> OTHER INFORMATION: D-Lys

<400> SEQUENCE: 24

Xaa Cys Gln Gln Ser Tyr Ser Ile Pro Trp Thr Cys Lys Lys
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (4)..(4)
<223> OTHER INFORMATION: D-Gln
<220> FEATURE:
<221> NAME/KEY: MOD_RES
<222> LOCATION: (13)..(14)
<223> OTHER INFORMATION: D-Lys

<400> SEQUENCE: 25

Xaa Cys Gln Gln Ser Tyr Ser Ile Pro Tyr Thr Cys Lys Lys
1               5                   10
```

```
-continued

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (5)..(5)
<223> OTHER INFORMATION: D-Ser
<220> FEATURE:
<221> NAME/KEY: MOD_RES
<222> LOCATION: (13)..(14)
<223> OTHER INFORMATION: D-Lys

<400> SEQUENCE: 26

Xaa Cys Gln Gln Ser Tyr Ser Ile Pro Tyr Thr Cys Lys Lys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (6)..(6)
<223> OTHER INFORMATION: D-Tyr
<220> FEATURE:
<221> NAME/KEY: MOD_RES
<222> LOCATION: (13)..(14)
<223> OTHER INFORMATION: D-Lys

<400> SEQUENCE: 27

Xaa Cys Gln Gln Ser Tyr Ser Ile Pro Tyr Thr Cys Lys Lys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 28

Xaa Cys Glu Gln Ser Tyr Ser Ile Pro Tyr Thr Cys Lys Lys
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Aha

<400> SEQUENCE: 29

Xaa Cys Gln Glu Ser Tyr Ser Ile Pro Tyr Thr Cys Lys Lys
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 30

Xaa Cys Gln Gln Glu Tyr Ser Ile Pro Tyr Thr Cys Lys Lys
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 31

Xaa Cys Gln Gln Ser Glu Ser Ile Pro Tyr Thr Cys Lys Lys
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 32

Xaa Cys Gln Gln Ser Tyr Glu Ile Pro Tyr Thr Cys Lys Lys
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 33

Xaa Cys Gln Gln Ser Tyr Ser Glu Pro Tyr Thr Cys Lys Lys
1               5                   10
```

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 34

Xaa Cys Gln Gln Ser Tyr Ser Ile Glu Tyr Thr Cys Lys Lys
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 35

Xaa Cys Gln Gln Ser Tyr Ser Ile Pro Glu Thr Cys Lys Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 36

Xaa Cys Gln Gln Ser Tyr Ser Ile Pro Tyr Glu Cys Lys Lys
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 37

Xaa Cys Arg Gln Ser Tyr Ser Ile Pro Tyr Thr Cys Lys Lys
1               5                   10

<210> SEQ ID NO 38
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 38

Xaa Cys Gln Arg Ser Tyr Ser Ile Pro Tyr Thr Cys Lys Lys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 39

Xaa Cys Gln Gln Arg Tyr Ser Ile Pro Tyr Thr Cys Lys Lys
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 40

Xaa Cys Gln Gln Ser Arg Ser Ile Pro Tyr Thr Cys Lys Lys
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 41

Xaa Cys Gln Gln Ser Tyr Arg Ile Pro Tyr Thr Cys Lys Lys
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 42

Xaa Cys Gln Gln Ser Tyr Ser Arg Pro Tyr Thr Cys Lys Lys
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 43

Xaa Cys Gln Gln Ser Tyr Ser Ile Arg Tyr Thr Cys Lys Lys
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 44

Xaa Cys Gln Gln Ser Tyr Ser Ile Pro Arg Thr Cys Lys Lys
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha

<400> SEQUENCE: 45

Xaa Cys Gln Gln Ser Tyr Ser Ile Pro Tyr Arg Cys Lys Lys
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (6)..(6)
<223> OTHER INFORMATION: D-Tyr
<220> FEATURE:
<221> NAME/KEY: MOD_RES
<222> LOCATION: (13)..(16)
<223> OTHER INFORMATION: D-Lys

<400> SEQUENCE: 46

Xaa Cys Gln Gln Ser Tyr Ser Ile Pro Tyr Thr Cys Lys Lys Lys Lys
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: D-Lys
<220> FEATURE:
<221> NAME/KEY: MOD_RES
<222> LOCATION: (7)..(7)
<223> OTHER INFORMATION: D-Tyr
<220> FEATURE:
<221> NAME/KEY: MOD_RES
<222> LOCATION: (14)..(15)
<223> OTHER INFORMATION: D-Lys

<400> SEQUENCE: 47

Lys Lys Cys Gln Gln Ser Tyr Ser Ile Pro Tyr Thr Cys Lys Lys
1               5                   10                  15

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (2)..(2)
<223> OTHER INFORMATION: Pen
<220> FEATURE:
<221> NAME/KEY: MOD_RES
<222> LOCATION: (6)..(6)
<223> OTHER INFORMATION: D-Tyr
<220> FEATURE:
<221> NAME/KEY: MOD_RES
<222> LOCATION: (12)..(12)
<223> OTHER INFORMATION: Pen
<220> FEATURE:
<221> NAME/KEY: MOD_RES
<222> LOCATION: (13)..(14)
<223> OTHER INFORMATION: D-Lys

<400> SEQUENCE: 48

Xaa Xaa Gln Gln Ser Tyr Ser Ile Pro Tyr Thr Xaa Lys Lys
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sulfo-D-alanine
<220> FEATURE:

```
<221> NAME/KEY: MOD_RES
<222> LOCATION: (6)..(6)
<223> OTHER INFORMATION: D-Tyr
<220> FEATURE:
<221> NAME/KEY: MOD_RES
<222> LOCATION: (13)..(14)
<223> OTHER INFORMATION: D-Lys

<400> SEQUENCE: 49

Xaa Cys Gln Gln Ser Tyr Ser Ile Pro Tyr Thr Cys Lys Lys
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (13)..(14)
<223> OTHER INFORMATION: D-Lys

<400> SEQUENCE: 50

Xaa Cys Gln Gln Tyr Ser Tyr Leu Pro Ile Thr Cys Lys Lys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (13)..(14)
<223> OTHER INFORMATION: D-Arg

<400> SEQUENCE: 51

Xaa Cys Gln Gln Tyr Ser Tyr Leu Pro Ile Thr Cys Arg Arg
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (12)..(13)
<223> OTHER INFORMATION: D-Lys

<400> SEQUENCE: 52

Xaa Cys Gln Gln Ser Tyr Leu Pro Ile Thr Cys Lys Lys
1               5                   10
```

```
<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (12)..(13)
<223> OTHER INFORMATION: D-Lys

<400> SEQUENCE: 53

Xaa Cys Gln Gln Tyr Ser Leu Pro Ile Thr Cys Lys Lys
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (12)..(13)
<223> OTHER INFORMATION: D-Lys

<400> SEQUENCE: 54

Xaa Cys Gln Gln Tyr Asp Leu Pro Ile Thr Cys Lys Lys
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
<221> NAME/KEY: MOD_RES
<222> LOCATION: (13)..(14)
<223> OTHER INFORMATION: D-Arg

<400> SEQUENCE: 55

Xaa Cys Gln Gln Ser Tyr Ser Ile Pro Tyr Thr Cys Arg Arg
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Aha
<220> FEATURE:
```

-continued

```
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (14)..(15)
<223> OTHER INFORMATION: D-Arg

<400> SEQUENCE: 56

Xaa Cys Leu Gln Ala Leu Arg Thr Pro Leu Tyr Thr Cys Arg Arg
1               5                   10                  15
```